United States Patent [19]

Stock

[11] Patent Number: 5,770,793
[45] Date of Patent: Jun. 23, 1998

[54] METHOD FOR DETERMINING THE CONCENTRATION OF A SUBSTANCE IN A GAS

[75] Inventor: Burkhard Stock, Lübeck, Germany

[73] Assignee: Drägerwerk Aktiengesellschaft, Lübeck, Germany

[21] Appl. No.: 802,903

[22] Filed: Feb. 20, 1997

[30] Foreign Application Priority Data

Feb. 24, 1996 [DE] Germany .................. 196 07 062.7

[51] Int. Cl.$^6$ .................. G01N 21/35; G01N 33/98; G01N 33/497
[52] U.S. Cl. .................. 73/23.21; 73/23.3; 422/84; 436/900; 436/68; 250/343
[58] Field of Search .................. 73/1.06, 1.07, 73/23.2, 23.3, 31.03, 23.21; 422/84, 98; 436/68, 900, 132; 128/719; 180/272; 340/576; 250/343

[56] References Cited

U.S. PATENT DOCUMENTS 4,976,135  12/1990  Stock ........................................ 73/23.2
5,272,907  12/1993  Hakala ...................................... 73/23.2
5,279,795  1/1994   Hughes et al. ....................... 73/23.2 X
5,495,744  3/1996   Ueda et al. .............................. 73/1.07

OTHER PUBLICATIONS

"Alcohol, Drugs and Traffic Safety –T'95, vol. 1", G. Schoknecht et al, produced by NHMRC Road Accident Research Unit, The University of Adelaide 5005, Australia, 1995.

*Primary Examiner*—Michael Brock
*Attorney, Agent, or Firm*—Walter Ottesen

[57] ABSTRACT

The invention is directed to a measuring method for determining the concentration of a gas in a measurement sample with the aid of a combined measuring apparatus. The measuring apparatus includes a first infrared optical gas analyzer 1 as well as a second gas analyzer 2, which contains an electrochemical measuring cell 13. The measuring result of the electrochemical measuring cell 13 functions to correct the concentration, which is determined by the infrared optical gas analyzer 1, when the infrared optical reference measurement has already been performed on a measurement sample with this measuring sample not being free of the substance to be detected.

3 Claims, 1 Drawing Sheet

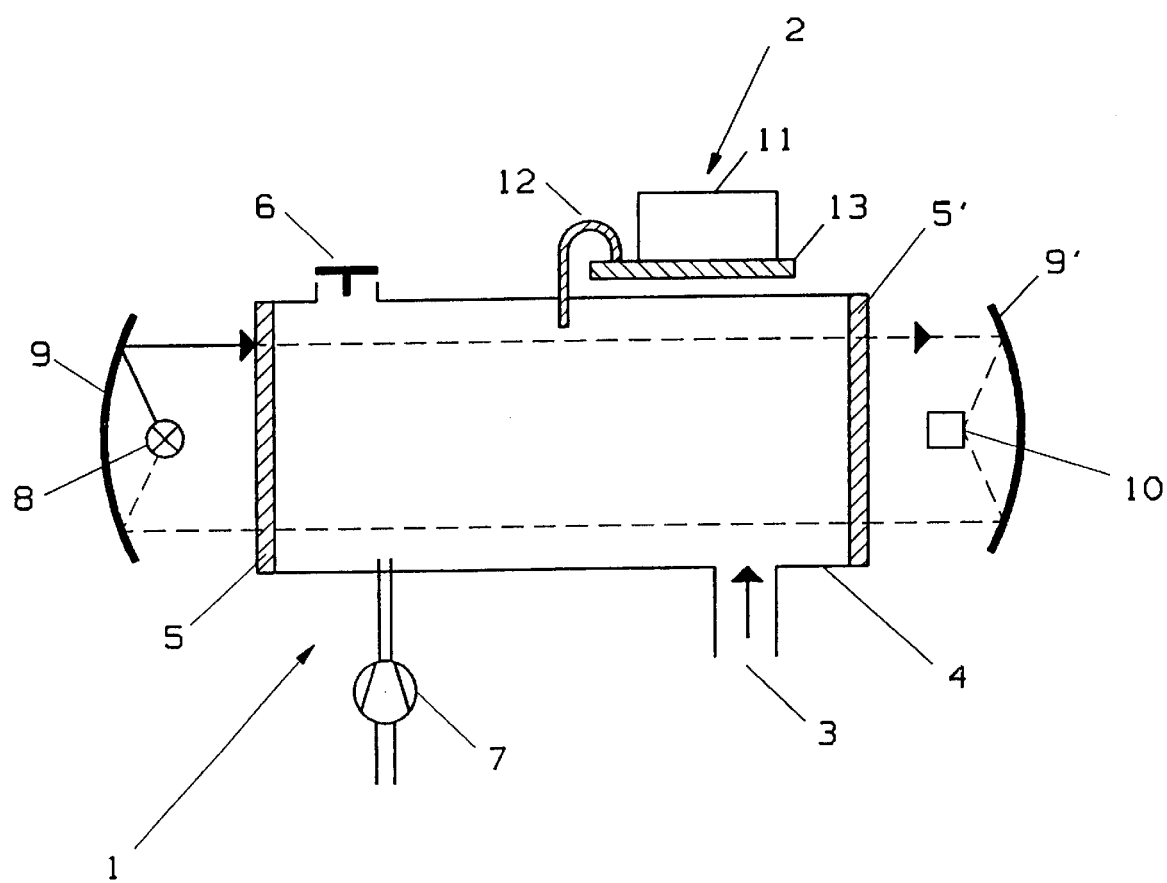

METHOD FOR DETERMINING THE CONCENTRATION OF A SUBSTANCE IN A GAS

FIELD OF THE INVENTION

The invention relates to a method for determining the concentration of a substance in a gaseous sample.

BACKGROUND OF THE INVENTION

Measurement methods of this kind are applied in order to, for example, determine the concentration of ethanol in the exhaled breath of a person. The publication entitled "Alcohol, Drugs and Traffic Safety-T'95", Volume 1 (1995), pages 134 to 140 (ISBN 0-908204-21-3) discloses a combination apparatus as a measuring device for making such determinations. This apparatus includes a first and a second gas analyzer to determine the alcohol concentration in a gaseous sample to be measured. The first gas analyzer operates on the basis of the measurement of infrared absorption specific to the substance and the second gas analyzer is an electrochemical measuring cell specific to the substance.

In this publication, the two gas analyzers are operated in parallel and independently of each other in order to determine measurement values with the two different methods and to then compare these measurement values.

In non-dispersive infrared gas analyzers, the relative attenuation of the light after passing through a measurement cuvette is a criterion for the gas concentration contained therein. The reference signal must be newly determined at suitable time intervals because the emitted radiation of the infrared radiator fluctuates as a consequence of deterioration and temperature changes.

This can happen in two ways as will now be described.

In the first way, directly before the measurement of the sample, a reference medium is introduced into the gas analyzer which is free of the substance (gas sample to be measured) to be determined. This reference medium is, as a rule, the ambient air for breath alcohol measuring apparatus. The reference radiation intensity $I_0$ measured in this manner is taken as a reference value for the subsequent measurement which supplies the signal $I_1$. The gas concentration c is computed from the Lambert-Beer Law for $I_0 \approx I_1$ via a series formation and termination after the linear member, that is only the linear term is used and the other terms are omitted. The gas concentration c is then computed from:

$$c = a \cdot \frac{I_0 - I_1}{I_0}$$

wherein:
- a=calibration factor which is determined by calibrating measurements on a sample of known concentration;
- $I_0$=measured radiation intensity in the absence of the gas to be measured (measurement gas);
- $I_1$=measured radiation intensity in the presence of the measurement gas.

If the reference medium is, however, already charged with the substance to be determined, then the reference is not valid and therefore the measurement result for the concentration of the substance to be determined in the gaseous measuring sample is incorrect. For breath alcohol measuring apparatus, this is, for example, possible when the ambient air is contaminated by the exhaled breath of the test person. Relief can be provided with a selective filter (active charcoal) with which contamination is removed from the reference medium. It is disadvantageous with filters of this kind that they more or less deteriorate rapidly as well as require additional handling.

The second way is to determine $I_0$ in that an infrared filter is pivoted into the beam path and the radiation passed therethrough is not influenced by the substance to be measured. The additional complexity and the required high mechanical stability of the filter exchange system is disadvantageous.

SUMMARY OF THE INVENTION

It is an object of the invention to provide a precise method, which is stable over time, for determining the concentration of a substance in a gaseous measurement sample wherein contamination of the ambient air with the substance to be determined is compensated. The ambient air serves as the reference medium. It is another object of the invention to avoid mechanical parts or a reference infrared channel.

The method of the invention is for determining the concentration of a substance in a gaseous sample to be measured, the substance also being in ambient air. The method utilizes a first gas analyzer for measuring infrared absorption of the substance and a second gas analyzer configured as an electrochemical measuring cell; the first gas analyzer including: a measurement cuvette having a gas inlet and a gas outlet; a pump connected to the cuvette for scavenging the latter; an infrared radiator for generating and transmitting infrared radiation through the measurement cuvette; and, an infrared radiation detector for receiving the infrared radiation transmitted through the cuvette; and, the second gas analyzer including a sample-taking line for connecting the second gas analyzer directly to the measurement cuvette; and, the method comprising the steps of: filling the measurement cuvette with ambient air and utilizing the second gas analyzer to draw a sample via the sample-taking line to analyze the ambient air and determine the concentration ($\Delta c$) of the substance in the ambient air; infrared-optically measuring the ambient air in the measurement cuvette to measure the infrared absorption ($I_0 - \Delta I_0$) thereof; emptying the measurement cuvette of the ambient air; filling the measurement cuvette with the gaseous sample; infrared-optically measuring the gaseous sample to measure the infrared absorption ($I_1$) thereof; and, determining the true concentration (c) of the substance in the gaseous sample by adding an apparent concentration (c') to the concentration ($\Delta c$) of the substance present in the ambient air wherein (c') is determined with the aid of the infrared absorption ($I_0 - \Delta I_0$) in the ambient air utilizing the relationship:

$$c' = a \cdot \frac{(I_0 - \Delta I_0) - I_1}{I_0}$$

wherein:
- a=calibration factor which is determined by calibrating measurements on a gaseous sample of known concentration of the substance.

The essential advantage of the invention is seen in that a measuring method is provided for a compact measuring unit which combines the characteristics of the electrochemical measuring cell with the proven measurement principle of infrared absorption. The characteristics of the electrochemical measuring cell are to supply a concentration-dependent measurement signal in response to the presence or concentration of a substance to be determined in a gaseous measurement sample and to supply this measurement signal directly and without a reference measurement.

BRIEF DESCRIPTION OF THE DRAWING

The invention will now be described with reference to the drawing which shows a measuring apparatus for carrying out the method of the invention.

DESCRIPTION OF THE PREFERRED EMBODIMENTS OF THE INVENTION

The assembly shown in the drawing essentially comprises the combination of a first gas analyzer 1 for measuring the concentration of the specific substance in the gas with the aid of infrared absorption as well as second gas analyzer 2 which is configured as an electrochemical measuring system, such as disclosed in U.S. Pat. No. 4,976,135 incorporated herein by reference. The gas to be analyzed reaches the measuring cuvette 4 via a gas inlet 3. The measuring cuvette 4 is closed at both ends by windows (5, 5').

During the analysis, the gas outlet 6 is closed via a check valve so that the gas to be analyzed cannot escape via diffusion. The pump 7 functions to scavenge the cuvette 4. At the start of a measurement, ambient air is first drawn by suction through the inlet 3 and into the cuvette 4. The check valve is closed. The radiation generated by the infrared radiator 8 is collected to form a beam by means of the first mirror 9 and then runs parallel through the measuring cuvette 4 and is deflected onto the infrared radiation detector 10 by a second mirror 9'. The infrared detector 10 outputs a corresponding measurement signal. The infrared detector may measure infrared absorption in the wavelength region of 3.4 µm or 9.4 µm.

The electrochemical measuring system, namely, the gas analyzer 2, comprises a sample-taking system 11 which takes a sample (usually approximately 1 cm³) of gas from the cuvette 4 via the sample-taking line 12. The line 12 opens via a bore directly into the measuring cuvette 4. The sample is taken for analysis in the electrochemical measuring cell 13 via a pump (not shown) which draws the sample from the cuvette 4 via suction.

This arrangement makes possible the analysis of individual gas samples by two different measuring systems. The measuring cell 13 supplies a measurement signal when the gas (for example, ethanol in air) is present. No reference measurement is necessary as in the case of the infrared optical gas analyzer and the electrochemical measuring cell 13 can therefore be utilized to analyze the ambient air for the infrared optical reference measurement. This takes place best after the pump 7 has drawn ambient air into the measuring cuvette 4. The sample-taking system 11 for the electrochemical measuring cell 13 is then started and draws a small quantity (approximately 1 cm³) via suction into the electrochemical measuring cell 13 in order to make a determination of concentration. The result is then used in order to correct the infrared measurement, that is, the true concentration of the substance to be tested is given as follows.

The measurement cuvette 4 is filled with a measurement sample and infrared-optically measured in correspondence to the method described above. If the ambient air is, however, contaminated with a gas concentration $\Delta c$, then a gas concentration $c'$ results which corresponds to the relationship:

$$c' = a \cdot \frac{(I_0 - \Delta I_0) - I_1}{I_0}$$

$$c' = a \cdot \frac{I_0 - (I_1 + \Delta I_0)}{I_0}$$

$$c' = c - \Delta c$$

wherein:

$\Delta I_0$ = intensity component by which $I_0$ is attenuated by the presence of a concentration $\Delta c$ in the ambient air; and, $c'$ is equal to the true gas concentration $c$ in the measurement sample reduced by the amount $\Delta c$.

The true concentration $c$ is obtained by adding a gas concentration $\Delta c$ (which was determined by the electrochemical measuring cell) to the measuring result.

Another possibility comprises interrupting the actual measurement of the measurement sample (for example, ethanol in the exhaled breath of a test person) when a specific pregiven limit value for the concentration of the substance (for example, ethanol in the ambient air) is exceeded.

According to another embodiment, the infrared optical measurement is only then made as described above when a pregiven limit value for the contamination of the ambient air has not been reached or there has not been a drop therebelow.

Another embodiment of the method of the invention is utilized to determine the concentration of breath alcohol. The given wavelengths are especially suitable because of the pronounced specific infrared absorption for the ethanol determination.

It is understood that the foregoing description is that of the preferred embodiments of the invention and that various changes and modifications may be made thereto without departing from the spirit and scope of the invention as defined in the appended claims.

What is claimed is:

1. A method for determining the concentration of a substance in a gaseous sample to be measured, the substance also being in ambient air, the method utilizing a first gas analyzer for measuring infrared absorption of said substance and a second gas analyzer configured as an electrochemical measuring cell;

said first gas analyzer including:
a measurement cuvette having a gas inlet and a gas outlet;
a pump connected to said cuvette for scavenging the latter;
an infrared radiator for generating and transmitting infrared radiation through said measurement cuvette; and, an infrared radiation detector for receiving said infrared radiation transmitted through said cuvette; and, said second gas analyzer including a sample-taking line for connecting said second gas analyzer directly to said measurement cuvette; and, the method comprising the steps of:
filling said measurement cuvette with ambient air and utilizing said second gas analyzer to draw a sample via said sample-taking line to analyze said ambient air and determine the concentration ($\Delta c$) of said substance in said ambient air;
infrared-optically measuring said ambient air in said measurement cuvette to measure the infrared absorption ($I_0 - \Delta I_0$) thereof;
emptying said measurement cuvette of said ambient air;
filling said measurement cuvette with said gaseous sample;

infrared-optically measuring said gaseous sample to measure the infrared absorption ($I_1$) thereof; and, determining the true concentration (c) of said substance in said gaseous sample by adding an apparent concentration (c') to the concentration ($\Delta c$) of said substance present in said ambient air wherein (c') is determined with the aid of said infrared absorption ($I_0 - \Delta I_0$) in said ambient air utilizing the relationship:

$$c' = a \cdot \frac{(I_0 - \Delta I_0) - I_1}{I_0}$$

wherein:

a=calibration factor which is determined by calibrating measurements on a gaseous sample of known concentration of said substance.

2. The method of claim 1, comprising the further steps of:

determining if said concentration ($\Delta c$) of said substance in ambient air is less than a pregiven concentration;

if so, then infrared-optically measuring said ambient air to obtain the infrared absorption ($I_0$) thereof;

then filling said measurement cuvette with said gaseous sample and infrared-optically measuring said gaseous sample to obtain the infrared absorption ($I_1$); and, determining the concentration (c) of said substance in said gaseous sample from the relationship:

$$c = a \cdot \frac{I_0 - I_1}{I_0}.$$

3. The method of claim 2, wherein said substance is ethanol and the measurement of the infrared absorption is in the wavelength region of 3.4 $\mu$m or 9.4 $\mu$m.

* * * * *